United States Patent [19]

Cognion et al.

[11] 4,242,235

[45] Dec. 30, 1980

[54] SUPPORTS FOR SILVER CATALYSTS UTILIZED IN THE PRODUCTION OF ETHYLENE OXIDE

[75] Inventors: Jean-Marie Cognion, Saint Genis Laval; Jacques Kervennal, Lyons, both of France

[73] Assignee: Produits Chimiques Ugine Kuhlmann, Paris, France

[21] Appl. No.: 953,940

[22] Filed: Oct. 23, 1978

[30] Foreign Application Priority Data

Dec. 22, 1977 [FR] France .................................. 77 38744

[51] Int. Cl.$^3$ .......................... B01J 21/12; B01J 21/04; B01J 23/50
[52] U.S. Cl. ................................ 252/455 R; 252/463; 252/476; 260/348.34
[58] Field of Search .................... 252/455 R, 463, 476; 260/348.34

[56] References Cited

U.S. PATENT DOCUMENTS

| | | | |
|---|---|---|---|
| 3,664,970 | 5/1972 | De Maio | 252/476 X |
| 3,725,307 | 4/1973 | Brown et al. | 252/455 R |
| 4,010,115 | 3/1977 | Nielsen et al. | 252/476 X |
| 4,066,575 | 1/1978 | Winnick | 252/476 X |

FOREIGN PATENT DOCUMENTS 2723918 12/1977 Fed. Rep. of Germany .

Primary Examiner—Carl F. Dees
Attorney, Agent, or Firm—Pennie & Edmonds

[57] ABSTRACT

Silver catalysts for vapor phase synthesis of ethylene oxide by reacting oxygen or gaseous mixtures containing same with ethylene, characterized by the use as support of a porous material having a specific surface area of less than 10 sq. m/g, a total volume of porosity of between 0.1 and 0.6 cm$^3$/g and a bimodal distribution of the porosity.

13 Claims, 1 Drawing Figure

SUPPORTS FOR SILVER CATALYSTS UTILIZED IN THE PRODUCTION OF ETHYLENE OXIDE

BACKGROUND OF THE INVENTION

The present invention relates to supports for silver catalysts used in the vapor phase epoxidation of olefins and more particularly for the production of ethylene oxide from ethylene and molecular oxygen.

The production of ethylene oxide is carried out in the vapor phase in fixed bed tubular reactors by reacting oxygen and ethylene over silver catalytic phases which are deposited onto refractory and inert supports. These supports are made mainly of alumina, silica-alumina, magnesia, pumice stone, zirconia, clay, ceramics, natural or artificial graphite, asbestos, natural or artificial zeolite, or silicon carbide. Prior art shows a preference for solids with low specific surface areas. All the claimed supports have surface areas of less than 10 sq. m/g. Thus, in French Pat. No. 2,253,747, a whole series of porous products are mentioned, namely: silicon carbide, zirconia, silica, silica-alumina, α-alumina, with surface areas of between 0.04 and 10 sq. m/g. Specific surface areas in the same region: 0.03 to 10 sq. m/g, are also claimed in French Pat. Nos. 2,117,183; 2,130,465; 2,167,728; 2,249,087; and 2,271,869 using commercially available alumina or silica-alumina based supports. In fact, the specific areas of the supports employed are distinctly lower and figures of less than 1 sq. m/g are claimed in French Pat. Nos. 2,243,193 (alumina, silicon carbide, silica-alumina) and 1,522,279 (silica-alumina). These specific surface areas are determined in the majority of cases by the method of nitrogen adsorption, known as the B.E.T. method, described by BRUNAUER, EMMET and TELLER in "The Journal of the American Chemical Society", vol. 60, page 309, 1938. The second important property of these supports is their porosity. There is agreement in the prior art that a porosity which may reach 60 percent by volume is favorable to the activity and selectivity for ethylene oxide of the catalysts obtained. On the other hand, a certain divergence exists in the claims regarding the dimensions of the pores. The extent or degree of divergence is shown distinctly by the following figures:

I. 0.2 to 0.4 microns in French Pat. No. 2,249,087
II. 1 to 15 microns in French Pat. Nos. 2,253,747; 2,117,183 and in Belgian Pat. No. 848,659 for alumina or silica-alumina supports with low particle size
III. 50 to 200 microns in French Pat. Nos. 1,354,391 and 1,413,213 for alumina or silicon carbide supports having a large particle size which may reach as much as 9 mm
IV. 10 to 300 microns in French Pat. Nos. 2,243,193; 2,023,984; and 2,208,713 and in British Pat. No. 1,133,484
V. 50 to 1,500 microns in French Pat. Nos. 2,029,751; 2,059,124 and Czech Pat. No. 130,654, for supports on the basis of alumina with a high particle size which may be as much as 9 mm.

The importance of the relationship between the diameter of the pores and the particle size of the catalysts for the synthesis of ethylene oxide has been pointed out in two patents: French Pat. No. 2,253,747, which points out that the increase in the particle size of the silica-alumina supports must be accompanied by an increase in the mean diameter of the pores, and French patent application No. 77/21118, which claims, in the case of artificial graphite supports, the beneficial effect of an increase in the diameter of the macropores with the particle size.

SUMMARY OF THE INVENTION

The applicants have discovered in the present invention that the catalytic epoxidation of ethylene in a fixed bed can be carried out with very good selectivities if one uses as supports porous materials with a specific surface area of less than 10 sq. m/g, with a total volume of porosity which may reach 60 percent by volume, with a particle size which is greater than 1 mm and possessing a bimodal distribution of the porosity for the active phases of silver compounds. Such a distribution means that the support porosity consists of two groups of pores which differ in their diameter.

The applicants disclose that for catalysts used in a fixed bed with a particle size of between 1 and 15 mm, and more particularly between 3 and 10 mm, the coexistence of two ranges of porosity consisting of pores of different diameters was favorable to the selectivity for ethylene oxide. The mean diameter of the pores forming these two ranges of porosity is on the one hand in the range from 1 to 5 microns and on the other hand in the range from 60 to 200 microns. Each of these two ranges of porosity represents preferentially at least 35% and at most 65% of the total porosity.

The superiority of the catalysts to which the present invention relates has been clearly shown by comparative tests on three supports marketed by the firm NORTON under the tradenames SA 5239, SA 5151 and SA 5205, of which only SA 5239 possesses a bimodal distribution of the porosity and illustrates the present invention in a non-restrictive manner. The properties of these supports are set out in Table 1 and are shown in FIG. 1 which gives the variation in the volumes of porosity, expressed in $cm^3/g$ plotted against the diameter of the pores, expressed in microns.

TABLE 1

| | | | | |
|---|---|---|---|---|
| | | \multicolumn{3}{c}{$V_p$: volume of porosity} |
| | | \multicolumn{3}{c}{$R_M$: mean radius of pores} |
| SUPPORT | | SA 5239 | SA 5151 | SA 5205 |
| Shape | | Spheres | Extruded | Spheres |
| Particle size | | ¼ inch (6.4 mm) | ¼ × ¼ inch (6.4 × 6.4 mm) | ¼ inch (6.4 mm) |
| $Al_2O_3$ | % | 86.4 | 99.3 | 86.1 |
| $SiO_2$ | % | 12 | 0.4 | 11.8 |
| CaO | % | 0.2 | 0.1 | 0.4 |
| $Na_2O$ | % | 0.4 | 0.1 | 0.4 |
| $K_2O$ | % | 0.2 | — | 0.6 |
| Specific surface area BET (sq. m/g) | | 0.30 | 0.20 | 0.30 |
| POROSITY: | | | | |
| Vp total ($cm^3/g$) | | 0.340 | 0.270 | 0.100 |
| Vp (R = O, 25-5μ) | | 0.160 | 0.240 | 0 |
| | | (47%) | (89%) | 0 |
| Vp (R = 5–100 μ) | | 0.180 | 0.030 | 0.100 |
| | | (53%) | (11%) | (100%) |
| $R_M$ of pores (μ) | | 0.7 and 50 | 2 | 55 |
| Figure: | | Support No. 1 | Support No. 2 | Support No. 3 |

These measurements of porosity were carried out by the method known as the mercury porosimeter, recommended by E. W. Washburn in the Proceedings of the National Academy of Sciences of the U.S.A., vol. 7, page 115, 1927, and described by L. C. Drake in Industrial and Engineering Chemistry, vol. 41, page 780, 1949 and in Industrial and Engineering Chemistry Analytical Edition, vol. 17, page 782, 1945.

The nature of the supports also is important. The present invention permits the use of refractory supports which are more or less good conductors, such as α-alumina, silica-aluminas, silicon carbide, zirconia or graphite. They may take the form of rings, pellets, broken lumps, spheres or extruded forms of satisfactory mechanical properties, which do not permit the formation of dust during the preparation, handling, or operation of the catalyst.

The specific surface areas of less than 10 sq. m/g are advantageously between 0.1 and 1 sq. m/g and the volumes of total porosity which may reach 60 percent by volume are preferably between 20 and 50%.

The preparation of these new silver catalysts does not pose any problem and may be carried out by any standard process. In particular, one may operate in a manner known to the technician in two stages: by the impregnation or coating of a silver compound in solution or suspension in a volatile solvent, followed by a treatment which permits the formation of the metal on the support.

The silver compounds used may be either salts: nitrate, formate, lactate, citrate, carbonate, oxalate, acetate, sulphate, propionate, maleate, malate, malonate, phthalate, picolinate, anthranilate, tartrate, glycolate, succinate, oxide, hydroxide, acetylide or cetenide, or else complexes of silver salts with nitrogenated and/or oxygenated molecules such as ammonia, acrylonitrile, pyridine, ethanolamine, ethylene diamine, or complexes of silver with organic molecules such as salicylic acid, salicylaldehyde, β-diketones and the β-keto esters. The principal solvents or suspension liquids used are water, acetone, the light alcohols, ether, pyridine, ethyleneglycol, diethyleneglycol or chlorinated solvents.

Techniques which make possible the conversion of these compounds into the metal or the oxide may be employed, for example, precipitation, chemical reduction, and thermal decomposition in an inert, oxidizing or reducing atmosphere.

The catalysts to which the present invention relates have been prepared preferably by a process comprising the following three stages:
(a) impregnation of the support with a solution of the chosen silver compound. This impregnation may be carried out either by immersion of the support in the solution, or by the continuous sprinkling of the support under reduced pressure and at a temperature which permits the immediate elimination of the solvent.
(b) drying of the impregnated support.
(c) thermal treatment of the product obtained so as to liberate the silver from the compound deposited on the support.

The possible addition of the usual alkaline or alkali-earth promoters is beneficial and may be carried out during the impregnation. It is thus possible to add to these catalysts, in the usual contents, of 0 to 2 percent by weight, one or more standard promoters of silver described in the prior art and selected, for example, from among the following elements:

K, Ca, Cs, Ba, Pt, Ni, Sn, Cd, Sr, Li, Mg, Na, Rb, Au, Cu, Zn, La, Ce, Th, Be, Sb, Bi, Ti, Pd, Ir, Os, Ru, Fe, Al.

Likewise, the applicants have observed that in a known manner certain halogenated derivatives of the hydrocarbons, when added in small quantities to the reagents, increase the selectivity of the catalysts described in the present invention. The use of 1,2-dichloro ethane, at a maximum concentration of 1 ppm per total volume of the gas, has been found to be particularly useful.

The comparative examples 1 and 2 clearly show the superiority of the catalyst prepared on a support possessing a bimodal porous distribution. Examples 3 to 10 below illustrate in a non-limitative manner the preparation and use of the catalysts according to the invention.

DETAILED DESCRIPTION OF THE PREFERRED EMBODIMENT

Figure 1:
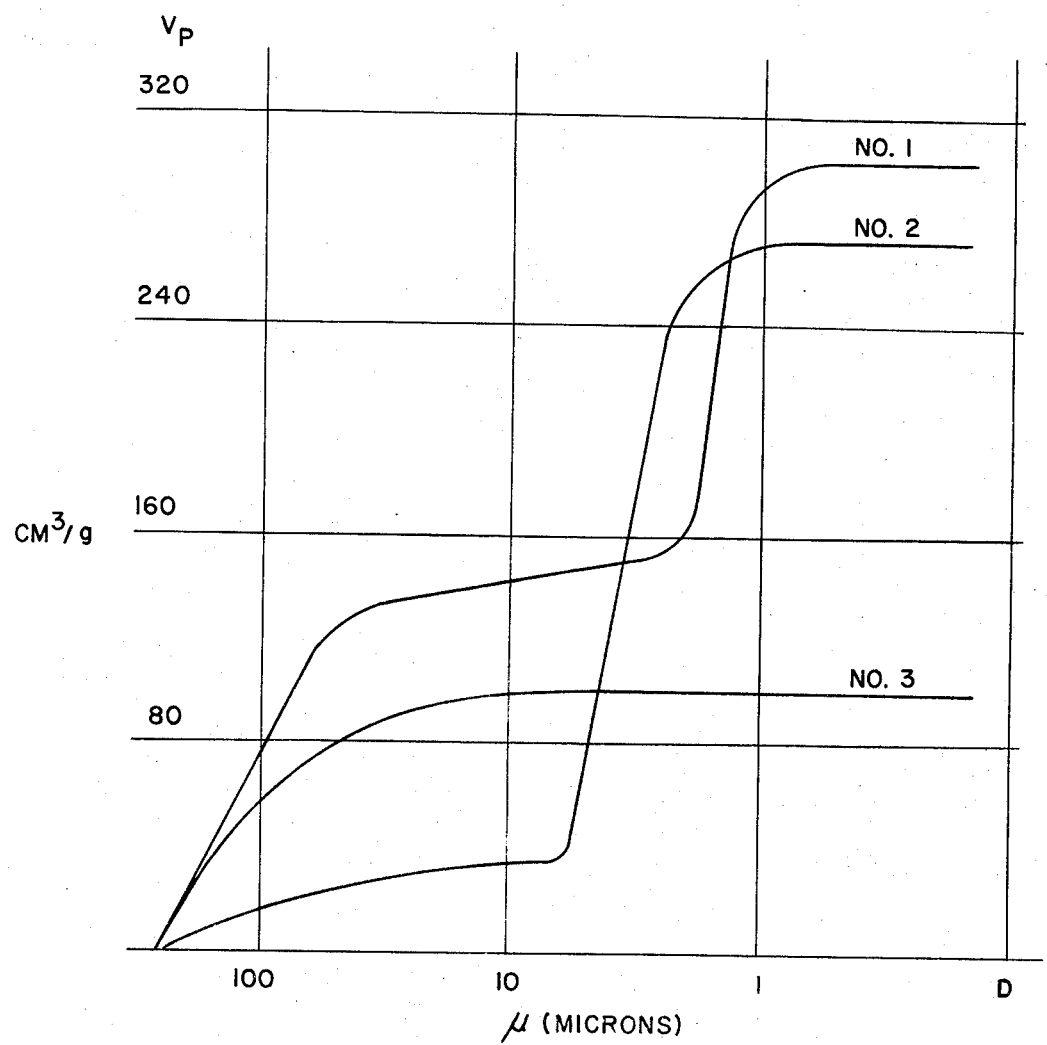
FIG. 1 is a drawing which gives the variation in the porosity volume expressed in cubic centimeters per gram plotted against pore diameters expressed in microns.

The results obtained in the below examples are expressed in rates of overall conversion of ethylene and in the selectivity for ethylene oxixde.

The overall conversion rate of ethylene (T.C.R.):

$$T.C.E. = \frac{\text{Number of moles of ethylene converted}}{\text{Number of moles of ethylene introduced}} \times 100$$

selectivity of the conversion into ethylene oxide (S.E.O.)

$$S.E.O. = \frac{\text{Number of moles of ethylene oxide formed}}{\text{Number of moles of ethylene converted}} \times 100$$

EXAMPLE 1

In a flask for solids, mounted on a rotary evaporator, one places 42.4 g of support SA 5151 manufactured by the NORTON Company and the properties of which are set out in Table 1 of FIG. 1. The temperature of the oil bath of the evaporator is maintained at 120° C., and the support is degassed for one hour under a partial pressure of 100 mm Hg. Under the same conditions of temperature and pressure, one then introduces drop by drop onto the agitated support a solution consisting of 11.7 g of silver acetate in 220 ml of pyridine. Under these conditions the evaporation of the solvent is instantaneous. After introducing the whole of the solution, the impregnated and dried support is transferred into a tubular reactor in order to undergo a thermal treatment which liberates the metal. This treatment is carried out for 18 hours under a stream of nitrogen with a temperature rise of 20° per hour up to 280° is achieved. Analysis of the catalyst shows a 13.3 percent by weight silver content.

Thirty ml of this catalyst is charged into a pressurized laboratory reactor. The reactor consists of a 355 mm long stainless steel tube with an internal diameter of 16 mm. It is heated by means of a molten nitrates bath. The reagents introduced through the bottom of the reactor are pre-heated over 42 mm of a procelain filling. The gases entering and leaving the reactor are analyzed in line by means of a double detection chromatograph: a flame ionization detector for the ethylene oxide, methane, formaldehyde, propylene, propane, methanol and acetaldehyde; and a thermal conductivity detector for oxygen-nitrogen, carbon dioxide, ethylene and water. The two columns ⅛ inch in diameter and, 2.5 meters long mounted in series and are filled, one with chromosorb 101, the other with porapak Q.

The catalyst is subjected to an activation pre-treatment with a 50%—50% ethylene-air mixture at atmospheric pressure for 35 hours at between 168° C. and 194° C. One then introduces, under a pressure of 20 bars, the reagents which consist of a mixture of 13% ethylene, 5% oxygen, 82% nitrogen and 35 parts per billion of 1,2-dichloro ethane, at a rate of flow at 9,000 normal liters per hour per liter of catalyst. At 190° C. one obtains a 4.1% overall rate of conversion for ethylene and a 71.2% selectivity for ethylene oxide.

EXAMPLE 2

One charges into a solids flask mounted on a rotary evaporator 29.5 g of support SA 5205, manufactured by the NORTON Company, the properties of which are set out in Table 1 and FIG. 1. Utilizing the procedure set forth in Example 1, one impregnates the support with a solution of 8 g of silver acetate in 200 ml of pyridine.

After the thermal treatment, catalyst analysis shows a silver content of 14.9 percent by weight. One charges 30 ml of this catalyst into the pressurized reactor as described in Example 1. An activation pre-treatment with a 50%—50% air-ethylene mixture is maintained for 36 hours at between 182° and 198° C. carried out at atmospheric pressure. One then introduces the reagents under 20 bars in the following proportions: ethylene 13%, oxygen 5%, nitrogen 82%, 1,2-dichloro ethane 35 ppb. The introductory gas flow rate is 9,000 normal liters per hour per liter of catalyst. At 199° C., one obtains a total conversion rate of 4.7% while the ethylene oxide selectivity is 72%.

EXAMPLE 3

One places in a solids flask mounted on a rotary evaporator 42.5 g of support SA 5239 manufactured by the NORTON Company the properties of which are set out in Table 1 and FIG. 1. This support is impregnated by the procedure described in Example 1 using a solution of 11.6 g of silver acetate in 220 ml of pyridine.

The silver content obtained after thermal treatment, carried out under the same conditions are those described in Example 1, is 12.5 percent by weight. One charges 30 ml of this catalyst into the test reactor described in Example 1 and one passes through for 29 hours at atmospheric pressure a 50%—50% ethylene-air mixture at between 160° and 176° C. One then introduces the reagents under 20 bars under the same conditions as those described in Examples 1 and 2. At 205° C., for a T.C.R. of ethylene of 5%, one obtains an ethylene oxide selectivity of 75% which is distinctly higher than those obtained in the two preceding examples.

EXAMPLE 4

Following upon test No. 3, one passes over the same catalyst charge, under a pressure of 20 bars, a gas stream consisting of 9,000 normal liters per hour and per liter of catalyst, consisting of ethylene, oxygen, nitrogen and various contents of carbon dioxide, as well as 35 ppb of 1,2-dichloro ethane. One obtains the results described in Table 2.

TABLE 2

| Entering gases | | | | Temperature (°C.) | T.C.R. ethylene (%) | S.O.E. ethylene oxide (%) |
| --- | --- | --- | --- | --- | --- | --- |
| % ethylene | % oxygen | % nitrogen | % CO$_2$ | | | |
| 13 | 5 | 72 | 10 | 221 | 5 | 75 |
| 13 | 5 | 68 | 14 | 221 | 5 | 73 |

EXAMPLE 5

The purpose of this Example is to study a catalyst which has a high silver concentration. One uses as support the silica/alumina balls marketed by the NORTON company under reference SA 5239.

One impregnates 36 g of this support under identical conditions to those described in Example 1 using a solution of 15 g of silver acetate in 300 ml of pyridine. After a thermal treatment identical to that described in Example 1, the determination shows a silver content of 20 percent by weight in the catalyst. One then charges 30 ml of the catalyst into the test reactor described in Example 1 and introduces over a period of 28 hours a 50%—50% ethylene-air gaseous mixture at atmospheric pressure at between 158° and 166° C. A gas stream of 9,000 normal liters per hour per liter of catalyst is passed into the reactor under a pressure of 20 bars. This stream consists of 13% ehtylene, 5% oxygen, 82% nitrogen and 35 ppb of 1,2-dichloro ethane. Under these conditions at 198° C., the total conversion rate of ethylene is 5% and the ethylene oxide selectivity is 76%.

EXAMPLE 6

The impregnation of the support with the silver compound may be carried out in either a purely organic or an aqueous medium. Thus, one introduces under conditions identical to those described in Example 1 a solution of 11.8 g of silver acetate in 220 g of a 50%—50% water-pyridine mixture onto a 29.5 g SA 5239 support.

After a thermal treatment identical to that described in Example 1, the silver content of the catalyst is analyzed to be 13 percent by weight. One charges 30 ml of the catalyst into the reactor described in Example 1 and one passes over it for 32 hours a 50%—50% air-ethylene mixture at atmospheric pressure at between 157° and 171° C. Under a pressure of 20 bars, a gas mixture consisting of 13% ethylene, 5% oxygen, 82% nitrogen and 35 ppb of 1,2-dichloro ethane is introduced at a rate of 9,000 normal liters per hour per liter of catalyst. At 204° C. the T.C.R. of ethylene is 5% and the ethylene oxide selectivity is 75%.

EXAMPLE 7

One impregnates SA 5239 support with a silver compound and a barium compound 36 g. The support is placed on a solid flask mounted on a rotary evaporator. By means to two pumps working in parallel, one introduces on the one hand a solution of 15 g of silver acetate in 285 ml of pyridine and on the other hand 20.4 ml of a solution of 1.07 g of barium acetate in 100 ml of water, the whole under a partial pressure of 100 mm of mercury, the oil bath of the evaporator being heated to 120° C. The thermal treatment is identical to that described in Example 1 and the determinations show that the silver content is 19 percent by weight and the barium content is 0.25 percent by weight. One then charges 30 ml of the catalyst into the reactor described in Example 1 and one introduces over 45 hours at atmospheric pressure a 50%—50% air-ethylene gas mixture at between 150° and 169° C. One then passes under a pressure of 20 bars a gaseous mixture at a rate of 9,000 normal liters per hour per liter of catalyst. This mixture consists of 13% ethylene, 5% oxygen, 82% nitrogen and 35 ppb of 1,2-dichloro ethane. At 180° C., one obtains a T.C.R. of ethylene of 4.5% and an ethylene oxide selectivity of 75%.

EXAMPLE 8

One prepares the silver complex with salicylaldehyde by adding to a solution of 10.8 g, or 0.06 moles, of silver nitrate in 50 ml of water a solution of 8 g, or 0.06 moles, of salicylaldehyde in 40 ml of ethanol. Drop by drop, a solution of 2.6 g of soda in 80 ml of water is added. At a pH of 7.7 a greenish yellow precipitate is formed which is filtered off. The filtrate is taken up, and one continues to add, dropwise, the solution of soda until the pH reaches 7.7 once again and a new precipitate appears. One collects the latter together with the preceding one and starts the operation again until the filtrate is exhausted. The addition of the soda must be carried out carefully so as to avoid a sudden transition to too basic a pH since this would cause the precipitation of silver oxide. After washing the precipitate several times with water and ethanol, one collects, after drying, 12.7 g of a green product containing 46.9 percent by weight of silver, as against a theoretical value of 47.1%. The molar yield is 87%. The product must be kept away from the air and the light, because it undergoes a slow decomposition. According to the mode of operation described in Example 1, one prepares a catalyst from a solution of 12.7 g of the silver complex of salicylaldehyde thus obtained in 200 ml of pyridine and 23.5 g of a SA 5239 NORTON support. The impregnated and dried support is transferred into a tubular reactor so as to decompose the complex in a stream of nitrogen to which one adds 1.5% of hydrogen. So as to control the reaction thermally, this treatment is carried out with a temperature rise of 20° C. per hour until one reaches a plateau of 18 hours at 280° C. Post treatment analysis shows a silver content of 20 percent by weight in the catalyst. One places 30 ml of this catalyst in a reactor consisting of a 16 mm inside diameter stainless steel tube 600 mm long. The reagents are admitted at the bottom and are pre-heated over a 200 mm high bed of porcelain rings which also supports the catalyst charge. The reactor is heated by oil circulation on the double jacket. The gases, when entering and leaving the reactor, are analyzed by means of a device similar to that described in Example 1.

One passes through the catalyst bed arranged in the reactor a 50%—50% air-ethylene mixture at atmospheric pressure for a period of 25 hours at a temperature of 190° C. One then introduces into the reactor at atmospheric pressure a stream of gas of 14 liters per hour, consisting of a mixture of 13% ethylene, 5% oxygen, 82% nitrogen and 640 ppb of 1,2-dichloro ethane. After 60 hours of operation, one obtains the results given in Table 3:

TABLE 3

| T °C. of the catalyst | % T.C.R. | % S.E.O. |
| --- | --- | --- |
| 180 | 5 | 76 |
| 194 | 10 | 73 |

EXAMPLE 9

The catalyst charge of Example 8 is transferred into the reactor operating under 20 bars described in Example 1. One introduces a gas stream with a specific hourly rate of flow of 9,000 normal liters per liter of catalyst, consisting of 13% ethylene, 5% oxygen, 82% nitrogen and 35 ppb of 1,2-dichloro ethane. After 27 hours of operation, one obtains at 206° C. a conversion of ethylene of 5% with a selectivity for ethylene oxide of 76%.

EXAMPLE 10

One prepares the silver salt of salicylic acid by adding a solution of 17 g, that is 0.10 moles, of silver nitrate in 30 ml of water to a solution of 13.8 g, that is 0.10 moles, of salicyclic acid in 200 ml of ethanol. One then runs slowly into the mixture 20 ml of a 5 N ammonia solution. The white precipitate which is immediately formed is washed with water, filtered and dried. One collects 23 g of silver salicylate corresponding to a molar yield of 94%. The silver content corresponds to theory: 44%.

According to the mode of operation described in Example 1, one prepares a catalyst from a pyridine solution of 18 g of silver salicylate prepared as above and 32 g of NORTON support SA 5239. After a thermal treatment identical to that described in Example 8, the determination shows a silver content of 11.2 percent by weight in the catalyst. One places 30 ml of this catalyst in the reactor described in Example 8 and one passes into it at atmospheric pressure for 14 hours a 50%—50% air-ethylene mixture at 215° to 250° C. One then introduces under atmospheric pressure 14 liters per hour of a gas containing 14% ethylene, 5% oxygen, 81% nitrogen, and 540 ppb of 1,2-dichloro ethane. After 28 hours operation, one obtains the results shown in Table 4.

TABLE 4

| T °C. of catalyst | % T.C.R. | % S.E.O. |
| --- | --- | --- |
| 206 | 5 | 77 |
| 227 | 10 | 74 |

Having described the invention with particular reference to the preferred form thereof, it will be obvious to those skilled in the art to which the invention pertains after understanding the invention, that various changes and modifications may be made therein without departing from the spirit and scope of the invention as defined by the claims appended hereto.

What is claimed is:

1. A process for the preparation of a supported silver catalyst suitable for the production of ethylene oxide comprising:
   (a) impregnating a porous refractory support material comprising:
      (1) a specific surface area of less than about 10 m$^2$/g,
      (2) a total porosity volume of between about 0.1 and 0.6 cm$^3$/g, and
      (3) a substantially bimodal porosity distribution in which:
         (a) the smaller pores have a mean diameter of about 1–5μ,
         (b) the smaller pores constitute about 35–65% of the pore volume, and (c) the larger pores have a mean diameter of about 60–200μ, with a liquid containing a compound or complex of silver, (b) drying the impregnated support, and (c) thermally treating the dried support to liberate the silver from the compound or complex deposited on the support.

2. The process of claim 1 wherein the smaller pores comprise about 45–55% of the pore volume.

3. The process of claim 1 wherein the support is selected from alumin or silica-alumina.

4. The process of claim 1 wherein the liquid is an aqueous solution.

5. The process of claim 1 wherein the liquid is a non-aqueous solution.

6. The process of claim 5 wherein the liquid comprises silver acetate and pyridine.

7. The process of claim 4 wherein the liquid comprises silver acetate and a 50%—50% water-pyridine mixture.

8. The process of claim 5 wherein the liquid is a pyridine solution of a silver complex with salicylaldehyde.

9. The process of claim 5 wherein the liquid is a pyridine solution of silver salicylate.

10. The process of claim 1 further comprising the addition of alkaline or alkali-earth promotors during impregnation.

11. The process of claim 10 wherein the concentration of the promotor is about 0 to 2 percent by weight.

12. The process of claims 1, 3 or 4 further comprising a barium compound selected from oxides or salts.

13. The process of claim 11 wherein the silver compound or complex is a salt.

* * * * *

UNITED STATES PATENT AND TRADEMARK OFFICE
CERTIFICATE OF CORRECTION

PATENT NO. : 4,242,235
DATED : December 30, 1980
INVENTOR(S) : Jean-Marie Cognion and Jacques Kervennal It is certified that error appears in the above-identified patent and that said Letters Patent are hereby corrected as shown below:

Residence of Jacques Kervennal reads "Lyons" should read
--Lyon--

Column 1, line 28 reads "specific areas" should read
--specific surface areas--

Column 6, Table 2 last heading reads "S.O.E. ethylene oxide" should read --S.O.E. oxide--

Column 9, line 14 reads "alumin" should read --alumina--

Signed and Sealed this

Thirty-first Day of March 1981

[SEAL]

Attest:

RENE D. TEGTMEYER

Attesting Officer

Acting Commissioner of Patents and Trademarks